(12) United States Patent
O'Rear et al.

(10) Patent No.: US 9,902,909 B2
(45) Date of Patent: Feb. 27, 2018

(54) PROCESS, METHOD, AND SYSTEM FOR REMOVING MERCURY FROM PIPELINES

(71) Applicant: Chevron U.S.A. Inc., San Ramon, CA (US)

(72) Inventors: Dennis John O'Rear, Petaluma, CA (US); Kevin J. Grice, Houston, TX (US); Vijay Ramchandra Pradhan, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 46 days.

(21) Appl. No.: 15/079,198

(22) Filed: Mar. 24, 2016

(65) Prior Publication Data

US 2016/0281005 A1    Sep. 29, 2016

Related U.S. Application Data

(60) Provisional application No. 62/138,063, filed on Mar. 25, 2015.

(51) Int. Cl.

| | | |
|---|---|---|
| *C10G 29/10* | (2006.01) | |
| *C02F 1/52* | (2006.01) | |
| *C07C 7/148* | (2006.01) | |
| *C02F 1/72* | (2006.01) | |
| *C10G 29/00* | (2006.01) | |
| *C02F 101/20* | (2006.01) | |

(52) U.S. Cl.
CPC ............ *C10G 29/10* (2013.01); *C02F 1/5236* (2013.01); *C02F 1/72* (2013.01); *C07C 7/1485* (2013.01); *C10G 29/00* (2013.01); *C02F 2101/20* (2013.01); *C10G 2300/205* (2013.01)

(58) Field of Classification Search
None
See application file for complete search history.

(56) References Cited

FOREIGN PATENT DOCUMENTS

| | | | |
|---|---|---|---|
| CN | 103120893 | * | 5/2013 |
| JP | 10024266 | * | 1/1998 |

* cited by examiner

*Primary Examiner* — Sheng H Davis
(74) *Attorney, Agent, or Firm* — Howard V. Owens (57) ABSTRACT

Hydroprocessing facilities may operate for extended periods of time before detection of mercury in the inlet facilities, as mercury adsorbs onto the metallic pipelines used to transport the hydrocarbon fluids, e.g., gas, produced waters, from the wells to processing facilities ("flowlines"). Once the pipelines become "saturated" with mercury, mercury will breakthrough and be detected at the inlet facilities. A mercury management/control scheme is disclosed wherein a chemical treatment step using aqueous sulfidic solution is integrated into a progressive pigging plan to clean the pipeline, managing mercury accumulation in the pipeline for a reduced mercury concentration in the fluid exiting the flowlines.

22 Claims, 3 Drawing Sheets

PROCESS, METHOD, AND SYSTEM FOR REMOVING MERCURY FROM PIPELINES

CROSS-REFERENCE TO RELATED APPLICATIONS

This application claims benefit under 35 USC 119 of U.S. Provisional Patent Application No. 62/138,063 with a filing date of Mar. 25, 2015 the disclosures are incorporated herein by reference in their entirety.

TECHNICAL FIELD

The invention relates generally to a process, method, system, and management plan for removal and control of heavy metals such as mercury accumulating on pipes.

BACKGROUND

Heavy metals such as mercury can be present in trace amounts in all types of produced fluids such as hydrocarbon gases, crude oils, and produced water. The amount can range from below the analytical detection limit to several thousand ppbw (parts per billion by weight) depending on the source. Mercury has been predominately managed with mercury removal adsorbent beds in facilities handling hydrocarbon gases, and by operationally managing mercury with mercury specific personal protection equipment ("PPE") and procedures.

Some gas processing facilities may operate for extended periods of time, e.g., years, before mercury is detected in the inlet facilities. It is known that mercury slowly accumulates in the flowlines from the wells to the gas processing facilities via adsorption. Once the flowlines become "saturated" with mercury, mercury will "breakthrough" and be detected at the inlet facilities. After "breakthrough," the rate of rise in mercury at the inlet facilities can be low, giving some notice time to implement a solution.

There is a need for a management scheme to/ leverage the flowline adsorption capacity to manage, control, and remove mercury in produced fluids from a reservoir, e.g., gas, crude, condensate, and produced water.

SUMMARY

In one aspect, the invention relates to a method to producing a produced fluid having a reduced concentration of mercury from a pipeline remove mercury contaminants from gas and/or crude productions. The method comprises: transporting a produced fluid containing mercury along the pipeline for a sufficient amount of time for the mercury to accumulate in the pipeline as elemental mercury, mercury sulfide and combinations thereof, wherein mercury accumulates on the pipeline for the produced fluid to reach a first mercury concentration at a check point downstream from an entry point of the produced fluid into the pipeline; stopping the transport of the produced fluid in a section of the pipeline; injecting a leading pig into the pipeline, wherein the leading pig is propelled by hydraulic pressure or flow of the produced fluid in the pipeline; injecting a composition comprising an aqueous sulfidic solution comprising at least 0.1 wt. % of any of a sulfide, a polysulfide, and combinations thereof, forming a first slug at rear of the leading pig, wherein the aqueous sulfidic solution reacts with elemental mercury, mercury sulfide, etc., accumulated on the pipeline along the first slug forming soluble mercury complexes; injecting a first trailing pig into the pipeline at rear of the first slug; and resuming flow of the produced fluid, for a produced fluid at a location of the pipeline downstream from the first slug to have a mercury concentration of less than 50% of the first mercury concentration.

In one embodiment, following the extraction of mercury from the flowline walls by chemical methods, the sulfidic solution is removed from the flowline by drainage or by flushing with a liquid (e.g., water, crude, condensate or a refined product).

DETAILED DESCRIPTION

The following terms will be used throughout the specification and will have the following meanings unless otherwise indicated.

"Flowline" refers to a pipe that transfers fluid from an oil or gas well to a processing facility. It might also transfer fluid from a smaller facility to a larger one within a given oil field.

"Pipeline" refers to a pipe that transfers gas, crude oil, gasoline or other finished product from a processing facility or storage facility to another location be it another processing facility, refinery, chemical plant or end user. As used herein, a pipe or pipeline refers to both flowline and pipeline, and pipeline is used interchangeably with flowline.

"Produced fluid" refers to any of hydrocarbon gases, crude oil, hydrocarbon condensate as well as mixtures of oil, gas and water in formation fluid that flows to the surface of an oil well from a reservoir.

"Trace amount" refers to the amount of mercury in the produced fluids. The amount varies depending on the source, e.g., ranging from a few $\mu g/Nm^3$ to up to 30,000 $\mu g/Nm^3$ in natural gas, from a few ppbw to up to 30,000 ppb in crude oil.

"Volatile mercury" refers to mercury that is present in the gas phase of well gas or natural gas. Volatile mercury is primarily elemental mercury (Hg) but may also include some other mercury compounds (organic and inorganic mercury species).

"Mercury salt" or "mercury complex" means a chemical compound formed by replacing all or part of hydrogen ions of an acid with one or more mercury ions.

"Mercury sulfide" may be used interchangeably with HgS, referring to mercurous sulfide, mercuric sulfide, and mixtures thereof. Normally, mercury sulfide is present as mercuric sulfide with an approximate stoichiometric equivalent of one mole of sulfide ion per mole of mercury ion. Mercury sulfide can be present in crystalline phases include cinnabar, metacinnabar and hypercinnabar with metacinnabar being the most common.

"Inorganic polysulfides" refer to compounds that dissolve in water to form $HS_x^-$ or $S_x^{-2}$ anions where x is equal to or greater than 2. Examples include sodium polysulfide, ammonium polysulfide, potassium polysulfide, calcium polysulfide, sulfanes ($H_2S_x$), When dissolved in water the inorganic polysulfides have a pH value greater than 7, for example greater than 9 or greater than 10. In one embodiment with the presence of polysulfides, oxidation of elemental Hg occurs to convert Hg into HgS, where the HgS is then dissolved in the high pH sulfidic solution to form mercury-containing aqueous sulfidic solution.

"Inorganic sulfides" refer to compounds that dissolve in water to form $HS^-$ or $S^{-2}$ anions. Examples include sodium sulfide ($Na_2S$), sodium sulfide nonahydrate ($Na_2S.9H_2O$), ammonium sulfide ($(NH_4)_2S$), ammonium bisulfide $NH_4HS$, sodium hydrosulfide (NaHS), and potassium, calcium and magnesium analogs. Examples also include $H_2S$ dissolved in water, preferably water with a pH greater than 7. When dissolved in water the inorganic sulfides have a pH value greater than 7, for example greater than 9 or greater than 10. In one embodiment with the presence of inorganic sulfides, HgS is dissolved in the high pH sulfidic solution to form mercury-containing aqueous sulfidic solution.

"Organic polysulfides" refers to compounds of the formula $RS_xR$, which do not dissolve appreciably in water to form $HS_x^-$ or $S_x^{-2}$ anions. Organic polysulfides can be hydrolyzed in caustic solutions to form $HS_x^-$ or $S_x^{-2}$ anions, and when used with caustic solutions, these are part of this invention.

"Anionic mercury complexes" refers to mercury species soluble in a aqueous solution of pH greater than 7 and containing inorganic sulfides or inorganic polysulfides that cannot be removed with a 1 micron filter. Examples of anionic mercury complexes include $HgS_xH^{-1}$ and $HgS_x^{-2}$ where x is greater than or equal to two.

Mercury-containing aqueous sulfidic solution refers to aqueous sulfidic solutions that contain dissolved mercury that cannot be removed by 1 micron filters. The mercury contents are greater than or equal to 10 ppbw; for example, greater than or equal to 100 ppbw; or for example, greater than or equal to 1000 ppbw.

Mercury-containing gas refers to a hydrocarbon gas that contains greater than or equal to 10 μg/Nm3 of mercury, e.g., greater than or equal to 100 μg/Nm3 of mercury.

Low-mercury content gas refers to a gas that contains less than 10 μg/Nm3 of mercury, e.g., less than or equal to 1 μg/Nm3 of mercury, less than or equal to 0.01 μg/Nm3 of mercury. In one embodiment, the low-mercury content gas is the gas at an inlet to an LNG facility after a treatment via a mercury removal unit (MRU).

Oxidation of aqueous sulfidic solutions refers contacting a mercury-containing aqueous sulfidic solution with an oxidant to remove the stabilizing sulfide ions and precipitate mercury sulfide. The oxidation can be done with a chemical oxidant, for example, hydrogen peroxide, hypochlorite, permanganate, or ferric salt. Or the oxidation can be done by air, for example in a wet air oxidation process.

Remote from wells refers to the distance from the gas or crude wells and the gas production facility. The distance is greater than or equal for 1 km, for example greater than or equal to 10 km; or for example greater than or equal to 100 km.

Methods for Hg Control/Removal—Chemical Approach: Mercury in a reservoir and the produced fluids from the reservoir typically exists in trace amounts in two primary forms: elemental mercury and particulate HgS. It is believed that elemental mercury vapor reacts in the reservoir with some of the sulfur species (e.g., mercaptans, disulfides, hydrogen sulfide, etc.), but does not react with thiophenes or aromatic sulfur compounds. The product from this reaction is nanometer-size particles of metacinnabar, forming micron-sized clusters in the hydrocarbon phase (and not to a large extent an aqueous phase). When the reactive sulfur species in the crude are consumed, elemental mercury does not react further and accumulates as such in the reservoir.

In one embodiment, an aqueous sulfidic solution containing compounds such as inorganic sulfides, inorganic polysulfides, or combinations thereof is used to remove accumulated mercury (mercury deposited and adsorbed onto the flowline). The solution can also be used to reduce the mercury arriving onshore in gas production facilities, to aid in the removal of accumulated liquid elemental mercury from flowlines during pigging, reducing decommissioning expenditures for mercury-contaminated flowlines at the end of their service life.

In one embodiment with the mercury in the flowline being primarily in the form of mercuric sulfide (HgS), an aqueous solution comprising inorganic sulfides is employed for the mercury removal. Mercuric sulfide dissolves in the presence of sulfidic solutions to yield soluble, e.g., anionic, mercury complexes of $HgS_xH$, $HgSx^{-2}$ and combinations thereof, wherein x>=2 (e.g., $HgS_2H$— and $HgS_2^{-2}$):

In one embodiment, with mercury in the flowlines being primarily in the form of elemental mercury ($Hg^0$), an aqueous solution comprising inorganic polysulfides ($M_2Sx$) is employed for the mercury removal. Inorganic polysulfides can oxidize mercury to the +2 state to be dissolved in the sulfidic solution to form anionic mercury complexes. Inorganic polysulfides consist of clusters with 2 to 10 or more sulfur atoms with a formal divalent negative charge. The clusters are in dynamic equilibrium and can grow or shrink. On average they have about four sulfur atoms. An example of the reaction with elemental mercury and one member of the polysulfides is shown below.

Thus depending on whether the mercury deposits as mercuric sulfide or elemental mercury, inorganic sulfides or inorganic polysulfides or mixtures thereof may be employed. In one embodiment, mixtures of the two sulfidic solutions are used. In another embodiment, the sulfidic solutions are used in sequence, e.g., an inorganic polysulfide can be used first to remove the liquid elemental mercury followed by an inorganic sulfide to remove the mercuric sulfide that was initially there, or formed by the oxidation of elemental mercury by the polysulfide.

The concentration of sulfide (or polysulfide) in the aqueous solution to remove mercury from the flowlines is least 0.1 wt % in one embodiment, for example, at least 0.5 wt %; between 1 and 25 wt %; and between 5 and 15 wt %. The maximum concentration should controlled as not to damage the flowline due to the high pH or direct action of the sulfide. In one embodiment and depending on the material of construction of the pipeline, the pH of the aqueous solution is adjusted to a level of less than 9 with the addition of mineral or organic acids.

Methods for Hg Control/Removal—Thermal Approach: In one embodiment, in addition or in place of the removal of mercury in flowlines with aqueous sulfidic solutions, mercury absorbed or deposited on the pipeline is removed by a thermal approach, e.g., via laser and /or combustion and/or induction heating means. The application of heat vaporizes the elemental mercury and thermally decomposes the mercuric sulfide to vapor phase elemental mercury which can be swept away with a gas, or collected via a vacuum. The thermal decomposition of mercuric sulfide has been found to obey first order kinetics. The rate of decomposition is faster at higher temperatures, e.g., greater than 400° C., for a mercury removal rate of greater than 75%. In one embodiment, the thermal decomposition is carried out at a temperature of greater than 300° C. In one embodiment, the interior surface temperature of the pipeline is heated to at least 300° C., e.g., at least 350° C., at least 500° C. In one embodiment, the temperature is maintained at least 400° C. for at least 5 seconds. In another embodiment, it is maintained at least 400° C. for at least 1 minute. In yet another embodiment, the treatment was for at least 5 minutes for a mercury removal of at least 95% from the pipeline.

In one embodiment of the combustion method, a hydrocarbon is combusted with air or a mixture of air diluted with an inert gas. The hydrocarbon can either be a residue left on the walls of the pipeline, or can be a gas or liquid supplied to the flowline. The combustion can be controlled by feeding the air to a pig with burners.

In one embodiment with the use of laser, a mobile laser system with a source to generate laser beams which are transferred to a laser head (e.g., ("a thermal pig" or a "laser pig"), and which laser head in turn applies the laser beam to the pipe wall to clear/remove mercury on the pipe wall. The laser source in one embodiment has a power of at least 5 kW and a wavelength of at least 800 nm. In another embodiment the laser source has a power of at least 15 kW. The mobile laser source applies a laser cable having a length sufficient to traverse the length of the pipeline for mercury removal, e.g., greater than 1 mile in one embodiment. The laser cable in one embodiment has a high power optical fiber with a core having a diameter of greater than about 100 µm. Multiple fibers can be employed to convey the high power laser energy to a laser pig, which laser pig optionally conveys back information and data through the optical cable.

In one embodiment, the thermal pig employs an induction device with a magnetic flux control coil capable of heating the internal surface of the pipe to at least 400° C., generating up to 1 kW of energy. In yet another embodiment, a thermal pig in the form of a moving induction coil having capacity of up to 50 kW is employed to heat the internal surface of the pipe to at least 1000° C. at a rate of 4 mm/second. The use of magnetic flux control coil allows the target temperature to be controlled for a limited depth penetration at high frequency. With the use of a hollow induction coil, a flow of gas can still be possible to push the mercury vapors along the pipe.

Mercury Management/Removal Scheme: In one embodiment, mercury in the pipeline is allowed to adsorb/deposit onto the walls of a flowline, e.g., a pipeline, that runs from the well(s) to the processing facility. The mercury is allowed to accumulate for a given time set, e.g., by a turnaround maintenance schedule and/or until the mercury level at the production facility reaches a pre-determined limit due to substantial build-up of mercury in the pipeline. Once a sufficient amount mercury breakthrough is detected at the inlet facilities (or the predetermined time has elapsed), the operation is stopped for mercury removal with either chemical treatment and/or thermal treatment. The pre-determined limit can be a limit such that exceeding such a limit over a certain period of time would necessitate actions including installation of mercury removal units, procedures and processes to meet safety and environmental regulations and the like.

In one embodiment, at least a chemical treatment step is used in conjunction with a progressive pigging technique, with the use of a plurality of pigs ("pig train") to help contain the liquid in a column form within the pipeline, with each pig being used to create a "pig slug" mass. As used herein the term "pig" is to be given its broadest possible meaning and includes all devices that are known as or referred to in the pipeline arts as a "pig," a device that is inserted into and moved along at least a portion of the length of a pipeline to perform activities such as inspecting, cleaning, measuring, analyzing, maintaining, welding, assembling, or other activities known to the pipeline arts. The pig can be driven through the pipeline with hydraulic pressure, or it can be propelled by the pressure of a fluid, e.g., the produced fluid (or gas) flowing in the pipeline, the aqueous sulfidic solution, or a flushing solution. The pig can also be pulled along by a cable, e.g., a cable which was laid down by a previous pig that moved by hydraulic pressure.

The pigs can be unitary devices, as simple as a foam or metal ball, or a complex multi-component device such as a magnetic flux leakage pig. In another embodiment, pigs are devices that travel along its length and are moved through the pipeline by the flow of the material within the pipe. In yet another embodiment, the pigs used can be for both utility and in-line/intelligent functions. Utility pigs for example are used for utility functions such as cleaning. Intelligent pigs may also perform functions such as instrumentation, supplying/conveying information on the condition of the pipeline, e.g., thickness, location, extent of problems with the pipeline.

The pig can be constructed of any resilient material which is resistant to swelling upon contact with produced fluids or moisture. Generally the shape of the pig conforms to the cross section or configuration of the flowline to be cleaned, e.g., either spherical or cylindrical. The pig can be configured for its size to be adjustable/adaptable to the pipeline opening. Different types of pigs can be used in a progressive pigging technique, e.g., pigs having a solid form for plugging the pipeline forming a column, pigs with wire brush for initial cleaning/removal of wax from the pipelines, pigs with spring loaded blades, etc.

In one embodiment for the transport of a produced fluid having a first concentration of mercury in a pipeline, after a sufficient amount of time for mercury to be adsorbed/deposit on the pipeline, the mercury content at certain intervals along the pipe line and/or an exit point downstream ("checkpoint") is monitored. Once the concentration of mercury at the checkpoint reaches a certain level, e.g., at least 50% of the first concentration, a cleaning of the pipeline by chemical or thermal methods can be initiated. In another embodiment, the cleaning can be initiated after a certain interval of time, e.g., according to maintenance schedule of every few months, every year, etc.

Optional Initial Cleaning Step with Pigs: In one embodiment prior to the chemical or thermal steps for the removal of mercury, the pipeline can be optionally cleaned by the use of a conventional pig. This initial pigging reduces the amount of wax, asphalt, and solids in the line, but leaves mercury compounds adsorbed on the walls of the flowline.

After the optional step of cleaning with a pig, mercury is removed from the flowline by either the chemical or the thermal method, and optionally follow by the other method (i.e., chemical followed by thermal, or thermal follow by chemical).

Chemical Hg Removal Step: In the chemical method, an aqueous sulfidic solution is pumped through the pipeline (after the optional step of pigging to clean the pipelines) to dissolve the deposited mercury and to clean the pipeline. The direction of the flow can be the same as the flow of the fluid in the pipeline, or in reverse. Flowline pig(s) are used in conjunction with the aqueous sulfidic solution for the removal of mercury. The pigs agitate the mercury deposit and assist in the dissolution of the mercury.

In one embodiment, an aqueous flushing solution is also used to displace the sulfidic solution and prevent mixing with normal flowline fluids and gases (the fluid being transported in the pipe line). For example, a sulfidic solution may be incompatible with the normal flowline fluids and gases, e.g., the flowline fluid may contain hydrate inhibitors and polysulfides can react with oxygen scavengers that are normally used in the inhibitors. In one embodiment, an aqueous flushing solution is used to prevent corrosion that may be caused by the use of the aqueous sulfidic solution. For example, polysulfides are effective in oxidizing and dissolving elemental mercury, they can oxidize to form elemental sulfur. Elemental sulfur can corrode cast iron pipes. To prevent the formation of elemental sulfur, a flushing solution can be used to displace the polysulfide.

In one embodiment, the sulfidic solution (e.g., polysulfide solution) and the and the flushing solution are blanketed prior to use to prevent oxidation, and keeping the dissolved oxygen content to below 10 ppm, e.g., below 1 ppm, or below 10 ppbw. In one embodiment, the dissolved oxygen concentration in the sulfidic solution is minimized by stripping the solutions with an inert gas, or by use of certain oxygen scavengers such as dithionites, hydrazine salts, N,N diethylhydroxylamine, guanidine salts, oximes, D-(-)-isoascorbic acid and combinations thereof, which do not react with polysulfides. Some oxygen scavengers react with the sulfidic solutions, especially polysulfides, causing the oxygen scavenger not to function for oxygen scavenging, or may affect the mercury removal reaction by the sulfide solution. Examples of scavengers which can react with polysulfide include bisulfites, sulfites, metabisulfites and hydroxylamines, which should be avoided.

In one embodiment, a series of pigs are used to segregate the aqueous sulfidic solution, flushing solution, and the fluids and gases (transported or flowing in the pipeline). More than one aqueous flushing solution can be used, or a series of aqueous flushing solutions (e.g., different concentration, different compositions) can be used in conjunction with the same or different aqueous sulfidic solutions being used in series. The flushing solution in one embodiment is water. In another embodiment, the flushing solution comprises mixtures of xanthan and other polysaccharides. In a third embodiment, the flushing solution comprises a metal formate to dewater/flush the pipe.

In one embodiment for a mercury control/management scheme, a new pipeline or a newly cleaned pipe is first washed with a sulfidic solution of low concentration (e.g., less than 0.5 wt %) prior to the flow of produced fluids, hydrocarbon fluids, etc., such than a scale or layer of iron sulfide is formed on the interior surface of the pipe. This sulfide scale is reactive to elemental mercury, thus will assist in a subsequent removal of the mercury. However, too much of residual sulfidic solution (with a high concentration of sulfidic solution) can lead to corrosion from elemental sulfur, but small amounts assist in lessening the subsequent mercury adsorption on the interior surface of the pipe.

In one embodiment after flushing the aqueous sulfidic solution through the pipeline, the solution containing mercury can be filtered to remove any precipitated elemental sulfur prior to wastewater treatment or for recycle/reuse for mercury removal from the pipeline. In one embodiment, prior to the filtering step, the solution containing mercury can be oxidized, neutralized, or stripped.

In one embodiment, the precipitation of HgS from the aqueous sulfidic solution is carried out with addition of acids to reduce the pH to below 8, e.g., below 7. Examples of acids include by are not limited to HCl, $H_2SO_4$, $HNO_3$ and organic acids, which releases the $H_2S$ and reduces the stabilizing sulfide ions. In one embodiment, the released $H_2S$ is used to reformulate the sulfidic solution, e.g., by dissolving it in a solution of NaOH in water or $NH_4OH$ in water.

Another option to precipitate HgS is to use ammonium sulfide or ammonium hydrosulfide. The aqueous sulfidic solution can then be stripped to remove both ammonia and hydrogen sulfide. This removes the stabilizing sulfide ion and HgS precipitates. The ammonia and hydrogen sulfide can be used to reformulate the sulfidic solution by dissolving them in water.

Thermal Step for Hg Removal: After the optional step of pigging to clean the pipelines, the pipeline is heated by either lasers, induction heating, or by combustion for the removal of mercury in the thermal method with a thermal "pig." The heat treatment vaporizes the elemental mercury and thermally decomposes the mercuric sulfide to elemental mercury.

After the treatment with a thermal pig, a flow of gas, e.g., an inert gas, is provided to sweep the mercury vapor from the pipeline, leaving a clean pipe. In one embodiment, a filter is placed downstream of the thermal pig to help capture any residual Hg vapor that is not entrained in the gas flow. In yet another embodiment, a mercury vapor analyzer (MVA) is provided with the thermal pig to measure the presence of any residual Hg vapor out of the cleaned piping. In yet another embodiment, a secondary heat source is used (in addition to the thermal pig) to trail the cleaning pig by a short distance to perform a "burn test," checking for residual Hg on the metal surface. Alternately, the thermal pig can be run again at lower energies in a secondary pass to perform the burn test.

The thermal pig employs a heat generation device such as a laser, a combustor, an induction device to supply heat to the pipe and decomposes HgS to elemental Hg. The thermal pig moves either in response to the gas pressure, or is pulled along by an optional cable, with an umbilical supplying power to a laser pig, or fuel and/or oxidant to a combustion pig. In one embodiment, a cooling umbilical is also provided with the thermal pig provided for the periodic cooling of the pig. The cooling umbilical may be provided with a cooling fluid such as nitrogen, sea water, and the like. In another embodiment, at least a refrigeration unit is used to cool and condense the released mercury vapor for subsequent removal.

In one embodiment with a laser pig, the umbilical comprises a fiber optic cable with a laser at the end of the pipe and the laser light is conveyed along the fiber optic cable. In another embodiment with a combustion pig, residual wax and/or asphalt that adheres to the wall of the pipe is used as a fuel, with the hot gases leaving the combustion pig acting to pre-heat downstream sections of the pipe.

Optionally a cold box (e.g., a refrigeration unit) is placed downstream of the thermal pig. The cold box acts to condense the elemental Hg into liquid elemental Hg. When the cold box contains sufficient liquid elemental mercury, it is removed from the pipeline, emptied, and returned to its location. The cold box can be moved independently of the thermal pig by a separate looped cable. The cold box can be emptied by accessing ports along the pipeline. The cold box can be sized to store/collect a sufficient amount of mercury prior to being emptied. For example, for a pipeline loading of up to 50 g/m² of Hg, a typical cold box is sized to collect up to 1.5 liter of Hg to clean up to 2000 m² of internal pipe surface before being emptied once a day (about 2 km of piping of 12" diameter pipeline).

In one embodiment of an operation with a thermal pig, the thermal pig can be positioned in pipeline at pigging access point and placed in starting positon with gas or fluid sending umbilical and pig down the line. At the start, the thermal pig is powered up and then retrieved via umbilical which pulls the pig toward the access point. The cold box can be retrieved when full and repositioned or sized to accommodate anticipated mercury accumulation. In one embodiment, cooling fluid (e.g., refrigerant or seawater depending on desired temperature) is used for the cold box and/or to cool the thermal pig (e.g., induction coil or laser unit). The power level can be adjusted for a final clean assessment (burn test) in a secondary run using a mercury vapor analyzer (MVA) unit.

After the thermal treatment, the elemental mercury vapor is swept/removed from the pipeline with a gas stream. When the gas stream containing mercury exits the pipeline, it can be captured by adsorption or absorption.

Post Hg Removal Steps: After the chemical and/or thermal treatment, the pipeline is put back into service. The produced fluid after treatment has a mercury concentration of less than 50% the mercury concentration of the produced fluid prior to the treatment in one embodiment; less than 25% in a second embodiment; less than 10% in a third embodiment; and less than 5% in a fourth embodiment, possibly obviating the need for mercury removal unit (MRU) in the processing facility, storage facility, or refinery downstream from the section(s) of pipeline being treated for mercury removal.

The produced fluid after treatment has a mercury concentration of less than 100 ppbw of total mercury in one embodiment; less than 50 ppbw of total mercury in a second embodiment; less than 20 ppbw of total mercury in a third embodiment; and less than 10 ppbw of total mercury in a fourth embodiment. The produced fluid after treatment has a mercury concentration of less than 50% of the mercury concentration of the pre-determined level in one embodiment; less than 30% of the pre-determined level in a second embodiment; and less than 10% of the pre-determined level in a third embodiment.

In one embodiment, if there is a large amount of mercury removed or for a long pipeline (e.g., at least 1 km in length in one embodiment, at least 10 km in another embodiment), the elemental mercury vapors may condense into liquid elemental mercury in cooler downstream sections of the pipeline creating potential plugging. To obviate the plugging, a cold box can be placed downstream of the pipeline or at intervals to condense liquid mercury. The gas is routed through the cold box and the mercury is allowed to condense in the cold box. When the cold box accumulates sufficient mercury, it is removed, emptied, and put back in service.

In one embodiment after a chemical treatment step, when the mercury-laden sulfidic solution slug reaches the production facility, the solution containing mercury is treated according to the regulations in effect at the site of the production facility. In one embodiment, the solution is injected into an underground formation, e.g., a depleted oil or gas reservoir. In another embodiment, mercury (as elemental mercury or mercury complexes) is first removed from the sulfidic solution prior to further treatment/disposal.

Mercury can be removed from the sulfidic solution by processes known in the art, e.g., ion exchange or by adsorption. In one embodiment, exchange resins are used for the removal of mercury (in an anionic form such as $HgS_2H—$) from the sulfidic solution. In another embodiment, a process selected from any of neutralization, oxidation, stripping, distillation and combinations thereof is used to destabilize the $HgS_2H—$ anions and cause HgS to precipitate. HgS has an unusual solubility relationship in sulfidic solutions and temperature, with solubility decreasing as temperature increases (see "Equilibria of Red HgS (Cinnabar) and Black HgS (MetaCinnabar) and their Saturated Solutions in the Systems $HgS—Na_2S—H_2O$ and $HgS—Na_2S—Na_2O—H_2O$ from 25-75° C. at 1 Atmosphere Pressure" by F. W. Dickson and George Tunell, American Journal of Science, Vol. 256, November 1958, p. 654-679). In one embodiment, some of the HgS is precipitated by heating the sulfidic solution. The HgS can then be removed by filtration, centrifugation and combinations. The recovered HgS is in the form of a wet paste, to be subsequently disposed by any of retorting to form elemental mercury, landfill, slurry and injection into an underground formation, or by mixing with cement or plastic to form an inert solid. The recovered elemental mercury from retorting can be use in acceptable commercial applications.

In one embodiment after a thermal treatment step, upon exiting the pipeline the mercury-containing gas can be treated with an adsorber or absorber to capture the mercury. Examples of adsorbents for use to capture mercury from the gas phase include but are not limited to carbons, sulfur-treated carbons, iodine-treated carbons, copper-sulfide adsorbents, zinc adsorbents, aluminum adsorbents, molecular sieves, and silver-impregnated molecular sieves. Examples of absorbents include sulfidic solutions to precipitate mercury as mercuric sulfide, for the resulting mercuric sulfide paste to be removed/disposed accordingly.

Figure 1:
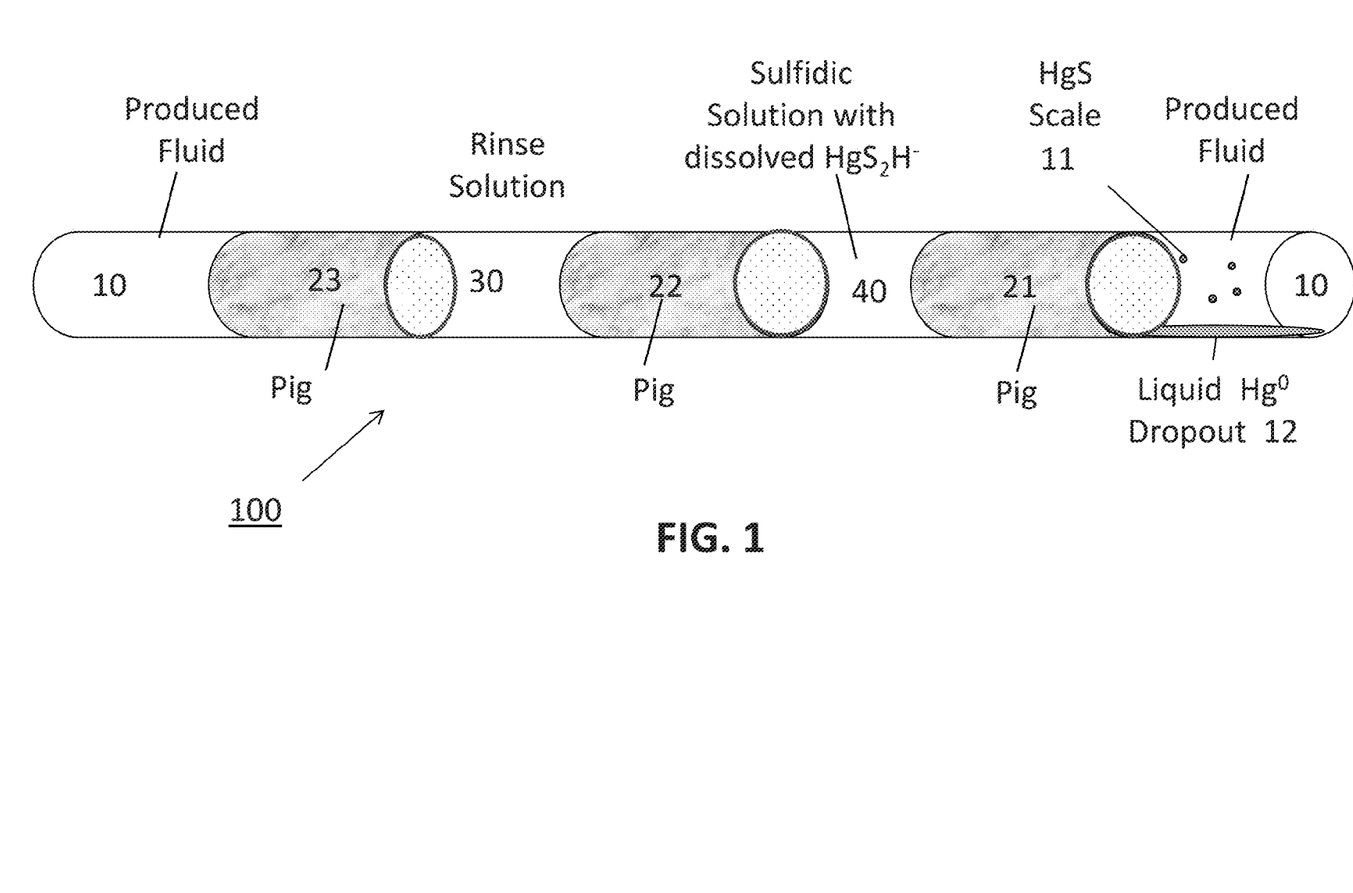
FIG. 1 is block diagram of an embodiment of a mercury management scheme using chemical treatment to remove mercury from a pipeline.

Figures Illustrating Embodiments: Reference will be made to FIG. 1 schematically shows a system and method for managing and removing mercury from a pipeline. In a pipeline 100 for the transport of produced fluid 10 which contains mercury complexes and scale 11 (e.g., HgS) and liquid mercury 12, a number of pipeline pigs 20 having a body with outer circumference matching the inner circumference of the pipeline 100 are used. A leading pig 21 is inserted into the pipe and is forced through the pipe by fluid pressure to create a pig slug mass. In one embodiment, the pig also cleans the pipe. The leading pig 21 can be a brush pig. As the leading pig 21 travels through the pipe, it scrapes deposits such as waxes, etc. from the interior wall of the pipe and transports the deposits along the pipeline. A plug comprising a sulfidic solution 40 is positioned to the rear of the pig for the removal of mercury absorbed/deposited onto the pipeline, dissolving mercury forming $HgS_2H—$ complexes. A trailing pig 22 follows the slug of sulfidic solution, and another plug with a rinse solution 30 is positioned to the rear of trailing pig 22 to displace the sulfidic solution 40 and prevent the mixing of the sulfidic solution 40 with the normal flowline fluid 30. Another trailing pig 23 follows the slug of rinse solution to separate and displace the rinse solution, allowing produced fluid 10 to the rear of the trailing pig 23 to move the pigs along the pipeline after being cleaned by a combination of the pigs and the aqueous sulfidic solution. "Clean" produced fluid 10 at the rear of trailing pig 23 can be recovered downstream for removal of mercury for recycle/treatment. The spacing between the first (21) and second (22) pigs can be set to provide enough sulfidic solution to dissolve the deposited mercury throughout most of the length of the pipe. Similarly, the spacing between the second (22) and third (23) pigs is sufficient to provide enough rinse solution to avoid incompatibility problems between the sulfidic solution and the produced fluid.

It should be noted that there can be a plurality of pigs and a plurality of columns within the pipeline, e.g., a column with corrosion inhibitors, etc., preceding the column/chemical treatment with sulfidic solution for mercury removal. Additionally, a series of pigs may be used instead as leading pig 21 for the cleaning of the pipe prior to treatment by chemical or thermal processes. In one embodiment (not shown), the flow is reversed for further cleaning of the pipeline.

Figure 2:
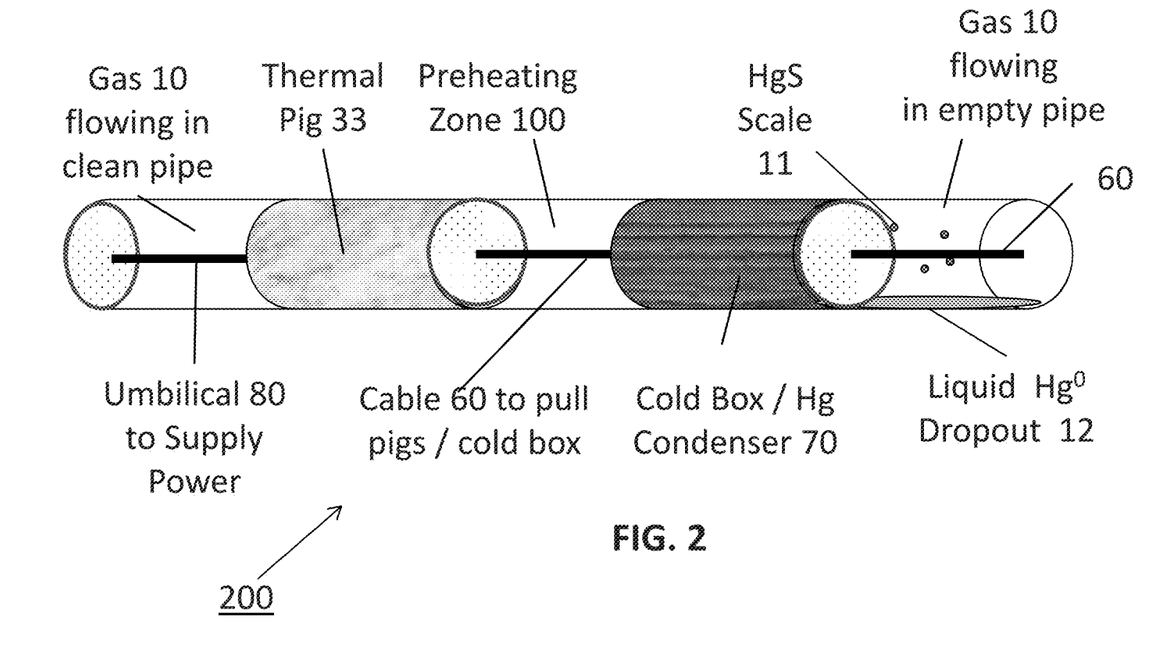
FIG. 2 is block diagram of an embodiment of a mercury management scheme wherein thermal treatment is employed to remove mercury from a pipeline.

FIG. 2 schematically shows another embodiment of a system and method for managing and removing mercury from a pipeline by the thermal process. In pipeline 100 for the transport of a gas 10 which contains mercury complexes and scale 11 (e.g., HgS) and liquid mercury 12, a thermal pig 33 in the form of a laser or a combustor, supplies heat to the pipe and decomposes HgS to elemental Hg. The thermal pig as shown is pulled along by cable 60. A cold box (Hg condenser) 70 is placed downstream of the thermal pig to condense the elemental mercury into liquid elemental mercury 12. When the cold box 70 contains sufficient liquid elemental mercury, it can be removed from the pipeline, emptied, and returned to the original location (not shown in figure). The cold box 70 can be moved independently from the thermal pig 33 by a separate loop cable (not shown). The cold box can be emptied by ports along the pipeline (not shown). Umbilical 80 is used to supply power to the thermal pig 33, e.g., to the laser, or used to provide/supply fuel and/or oxidant to the thermal pig 33. In one embodiment, the umbilical 80 is a fiber optical cable, wherein a laser is based at the end of the pipeline (not shown) and laser light is conveyed along the optic cable. In one embodiment, the hot gas 10 after being heated by the thermal pig functions to pre-heat downstream sections of the pipe.

Figure 3:
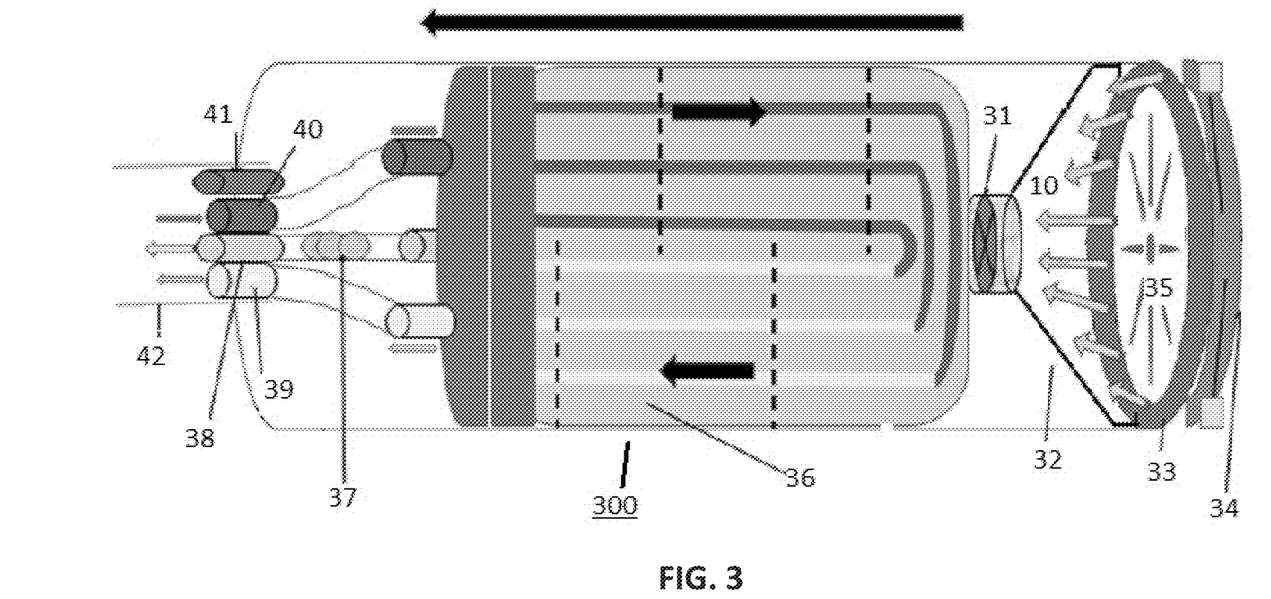
FIG. 3 is block diagram of yet another embodiment showing the use of a cold box in a thermal treatment scheme.

FIG. 3 is a diagram of a thermal treatment scheme with a cold box 300. The umbilical cord 42 houses various components including: power cord and accessories 41 needed for the thermal pig; inlet line 40 for cooling fluid (e.g., refrigerant or cold seawater); vapor/suction outlet 38; and outline line 34 for spent cooling fluid. Cold box is provided with an inlet with suction fan 31 and funnel 32 for pulling in gas containing mercury vapor 10. In one embodiment, a mercury vapor meter 35 is provided to monitor the level of mercury in the pipe. In yet another embodiment as shown, a mercury vapor trap (sorbent) 34 is provided. The thermal pig 33 can be any of a laser type or an induction coil.

EXAMPLES

The following illustrative examples are intended to be non-limiting

Examples 1-8

The examples illustrate the dissolution of HgS and $Hg^0$ in inorganic sulfidic solutions. In the examples, approximately 1/10 gram of metacinnabar powder (e.g., HgS from Alfa Aesar) or liquid elemental mercury (e.g., from Fisher Scientific) were placed in 40 ml VOA vials. 20 ml of 10% solutions of commercially available sodium sulfide, ammonium sulfide, sodium polysulfide, or ammonium polysulfide were added. The mixtures were shaken by hand for 30 seconds and then mixed for two minutes on a Vortex™ mixer. The solutions were allowed to stand undisturbed for fifteen minutes. Then the mercury content of the supernatant was measured by Lumex™ instrument. The results are summarized in Table 1.

TABLE 1

| Example | Hg Source | Amount, g | Inorganic Sulfide | pH | Observed Hg, ppm | % Dissolved |
|---------|-----------|-----------|-------------------|-------|------------------|-------------|
| 1 | HgS | 0.11 | Ammonium sulfide | 10.28 | 79 | 1.71 |
| 2 | HgS | 0.10 | Sodium polysulfide | 11.24 | 156 | 5.06 |
| 3 | HgS | 0.11 | Ammonium polysulfide | 11.23 | 323 | 7.96 |
| 4 | $Hg^0$ | 0.11 | Ammonium sulfide | 10.28 | 72 | 1.63 |
| 5 | $Hg^0$ | 0.10 | Sodium polysulfide | 11.24 | 164 | 5.33 |
| 6 | $Hg^0$ | 0.13 | Ammonium polysulfide | 11.23 | 302 | 6.29 |
| 7 | HgS | 0.12 | Sodium sulfide | 13.2 | 250 | 4.94 |
| 8 | $Hg^0$ | 0.10 | Sodium sulfide | 13.2 | 4 | 0.09 |

The results show that the mercury can be dissolved if sufficient solution is used, with solutions containing up to about 4500 ppm of mercury of either elemental mercury or mercuric sulfide dissolved in various sulfidic solutions.

Examples 9-44

The examples show the dissolution of mercury from impacted metal. In the examples, a steel plate from a commercial FSO (floating storage offloading) unit that had processed high mercury condensate for decades was tested. Previous analyses show that mercury resides in a surface scale is in the form of mercuric sulfide. The plate was cold cut using a band saw into 5 cm×5 cm coupons. Individual tests within the series consist of one set of parameters regarding solution strength and temperature (either 25° or 90° C.). To measure the effect of time, individual tests were stopped at 1, 6, or 24 hours.

Mercury concentrations were measured by a handheld XRF spectrometer. The XRF unit measures an area concentration of mercury ($\mu g/cm^2$). Total mercury (ppm) was a calculation of a real concentration ($\mu pg/cm^2$), times area ($cm^2$) and divided by the mass of the coupon. The mercury concentrations vary significantly between coupons, with the change in mercury related to the initial value for that coupon.

One coupon was placed into each of three 500 ml vessels each containing 150 ml of identical strength solution. Test Series were conducted at 25° C. and 90° C. on oscillating tables set to oscillate at 70 cycles per minute. During each series of testing, one coupon was extracted at each time interval rinsed, dried, and weighed. XRF analysis was performed to determine the residual mercury after cleaning for each of those coupons. Results are summarized in Table 2.

TABLE 2

| Example | Sulfidic Agent | Conc. Wt % | Temp, °C. | Time, Hours | Original Hg, ppm | Final Hg, ppm | % Removed |
|---|---|---|---|---|---|---|---|
| 9 | Na$_2$S | 2 | 25 | 1 | 46 | 3.2 | 93 |
| 10 | Na$_2$S | 2 | 25 | 6 | 12 | 1.9 | 84 |
| 11 | Na$_2$S | 2 | 25 | 24 | 24 | 1.3 | 95 |
| 12 | Na$_2$S | 2 | 90 | 1 | 29 | 1.6 | 94 |
| 13 | Na$_2$S | 2 | 90 | 6 | 45 | 2.0 | 96 |
| 14 | Na$_2$S | 2 | 90 | 24 | 52 | 1.7 | 97 |
| 15 | Na$_2$S | 10 | 25 | 1 | 35 | 1.7 | 95 |
| 16 | Na$_2$S | 10 | 25 | 6 | 20 | 0.6 | 97 |
| 17 | Na$_2$S | 10 | 25 | 24 | 70 | 1.6 | 98 |
| 18 | Na$_2$S | 10 | 90 | 1 | 55 | 1.5 | 97 |
| 19 | Na$_2$S | 10 | 90 | 6 | 33 | 0.9 | 97 |
| 20 | Na$_2$S | 10 | 90 | 24 | 27 | 0.2 | 99 |
| 21 | Na$_2$S$_x$ | 2 | 25 | 1 | 47 | 43.4 | 8 |
| 22 | Na$_2$S$_x$ | 2 | 25 | 6 | 32 | 29.2 | 9 |
| 23 | Na$_2$S$_x$ | 2 | 25 | 24 | 23 | 14.3 | 38 |
| 24 | Na$_2$S$_x$ | 2 | 90 | 1 | 30 | 27.1 | 10 |
| 25 | Na$_2$S$_x$ | 2 | 90 | 6 | 56 | 30.8 | 45 |
| 26 | Na$_2$S$_x$ | 2 | 90 | 24 | 62 | 48.8 | 21 |
| 27 | Na$_2$S$_x$ | 10 | 25 | 1 | 56 | 39.6 | 29 |
| 28 | Na$_2$S$_x$ | 10 | 25 | 6 | 53 | 49.8 | 6 |
| 29 | Na$_2$S$_x$ | 10 | 25 | 24 | 28 | 15.8 | 44 |
| 30 | Na$_2$S$_x$ | 10 | 90 | 1 | 40 | 30.1 | 25 |
| 31 | Na$_2$S$_x$ | 10 | 90 | 6 | 55 | 30.1 | 45 |
| 32 | Na$_2$S$_x$ | 10 | 90 | 24 | 44 | 18.8 | 57 |
| 33 | CaS$_x$ | 2 | 25 | 1 | 35 | 31.3 | 11 |
| 34 | CaS$_x$ | 2 | 25 | 6 | 71 | 75.6 | −6 |
| 35 | CaS$_x$ | 2 | 25 | 24 | 21 | 20.3 | 3 |
| 36 | CaS$_x$ | 2 | 90 | 1 | 123 | 130.1 | −6 |
| 37 | CaS$_x$ | 2 | 90 | 6 | 47 | 31.9 | 32 |
| 38 | CaS$_x$ | 2 | 90 | 24 | 10 | 10.8 | −8 |
| 39 | CaS$_x$ | 10 | 25 | 1 | 13 | 12.1 | 7 |
| 40 | CaS$_x$ | 10 | 25 | 6 | 113 | 113.8 | −1 |
| 41 | CaS$_x$ | 10 | 25 | 24 | 4 | 2.5 | 38 |
| 42 | CaS$_x$ | 10 | 90 | 1 | 21 | 28.4 | −35 |
| 43 | CaS$_x$ | 10 | 90 | 6 | 3 | 2.9 | 3 |
| 44 | CaS$_x$ | 10 | 90 | 24 | 72 | 32.7 | 55 |

Example 45

To simulate the removal of dissolved mercury from sulfidic solutions, mercury containing sulfidic solutions were prepared and processed by a series of chemical treatments. Sodium sulfide nonahydrate was diluted with deionized water to give a nominal 1 wt % solution. Metacinnabar was dissolved in the solution to give 1663 ppbw mercury.

Example 46

Three hundred grams of the solution from example 45 was placed in a three neck flask equipped with a stir bar, nitrogen purge of 300 cc/min and a to sampling port. The mercury could not be removed by a 1 micron filter. 37% hydrochloric acid was added in small amounts to convert the dissolved sulfide to hydrogen sulfide. The reaction was done at room temperature. The hydrogen sulfide was stripped out by the nitrogen purge. As the hydrochloric acid was added samples were withdrawn and analyzed for mercury by a Lumex analyzer. A portion of the sample was filtered through a 1 micron filter to determine the amount of particulate Hg in the sample. When the pH dropped to below 8, the mercuric sulfide precipitated and could be removed by the 1 micron filter. Results are summarized below in Table 3.

TABLE 3

| | Time, min | | | | | | | | | | |
|---|---|---|---|---|---|---|---|---|---|---|---|
| | 0 | 20 | 50 | 70 | 90 | 120 | 150 | 180 | 210 | 240 | 270 |
| pH | 12.03 | 11.79 | 11.7 | 11.65 | 11.23 | 10.7 | 7.98 | 7.95 | 7.8 | 7.34 | 6.79 |
| ml HCl | 0.00 | 0.50 | 1.00 | 1.50 | 2.00 | 2.50 | 3.00 | 3.25 | 3.50 | 4.00 | 4.50 |
| Hg in Aqueous, ppbw | 2,643 | 2,657 | 2,660 | 2,487 | 2,480 | 2,550 | 2,573 | 2,233 | 2,677 | 2,553 | 2,647 |
| Hg after Filter, ppbw | 2,737 | 2,550 | 2,633 | 2,523 | 2,600 | 2,177 | 157 | 90 | 73 | 42 | 48 |
| % Hg in Aqueous | 100 | 101 | 101 | 94 | 94 | 96 | 97 | 84 | 101 | 97 | 100 |
| % Hg filterable | −4 | 4 | 1 | −1 | −5 | 15 | 94 | 96 | 97 | 98 | 98 |
| % Hg Recovery | 100 | 101 | 101 | 94 | 94 | 96 | 97 | 84 | 101 | 97 | 100 |
| % Hg Loss | 0 | −1 | −1 | 6 | 6 | 4 | 3 | 16 | −1 | 3 | 0 |

Example 47

The example illustrates the removal of dissolved mercury from sodium sulfide solution by titration. In the titration, the mercury-containing aqueous sulfidic solution is brought in contact with an acid to remove the stabilizing sulfide ions and precipitate mercury sulfide. The titration can be done with any acid, such as hydrochloric acid, sulfuric acid, nitric acid, phosphoric acid, carbonic acid, acetic acid, and combinations thereof.

The final aqueous product from example 46 was filtered through a series of filters to determine the particle size distribution of the mercury precipitate. The filter size is preferably below 10 microns, e.g., below 5 or below 1. Results are shown below in Table 4.

TABLE 4

| Filter size, microns | (ppbw) | % Removed |
|---|---|---|
| 20 | 2267 | 14 |
| 10 | 1980 | 26 |
| 5 | 410 | 85 |
| 1 | 133 | 95 |

Example 48

Ammonium sulfide is an agent for removing mercury from flowlines. Metacinnabar was dissolved in a nominal 1 wt % solution of ammonium sulfide in deionized water to give 1663 ppbw mercury.

Example 49

The example illustrates the removal of dissolved mercury from ammonium sulfide solution by titration. The procedure of example 46 was repeated using the solution from example 48 with results shown below in Table 5. The final product was filtered through a 20 micron filter and the filtrate contained less than 50 ppbw mercury—the detection limit of the Lumex. When ammonium was the cation, the mercury was converted to a substantially filterable form when the pH dropped to below 9.5.

TABLE 5

| | Time, min | | | | | | | | |
|---|---|---|---|---|---|---|---|---|---|
| | 0 | 20 | 40 | 70 | 100 | 120 | 150 | 180 | 210 |
| pH | 9.6 | 9.49 | 9.18 | 9.15 | 9.14 | 8.97 | 8.66 | 8.31 | 5.72 |
| ml HCl | 0.00 | 0.50 | 1.00 | 1.50 | 2.00 | 3.00 | 4.00 | 5.50 | 7.50 |
| Hg in Aqueous, ppbw | 1,143 | 897 | 1,073 | 1,127 | 1,123 | 1,163 | 1,127 | 1,180 | 1,147 |
| Hg after Filter, ppbw | 1,143 | 149 | 111 | 130 | 106 | 109 | 108 | 53 | 12 |
| % Hg in Aqueous | 100 | 78 | 94 | 99 | 98 | 102 | 99 | 103 | 100 |
| % Hg filterable | 0 | 83 | 90 | 88 | 91 | 91 | 90 | 96 | 99 |
| % Hg Recovery | 100 | 78 | 94 | 99 | 98 | 102 | 99 | 103 | 100 |
| % Hg Loss | 0 | 22 | 6 | 1 | 2 | −2 | 1 | −3 | 0 |

Example 50

The example illustrates the removal of dissolved mercury from sodium sulfide solution by chemical oxidation. The procedure of Example 45 was used to prepare a mercury-containing sulfidic solution that contained 8,970 ppbw mercury. The procedure of Example 46 was followed, except that 30% hydrogen peroxide was substituted for hydrochloric acid. The hydrogen peroxide consumed the stabilizing SH— anion, resulting in precipitation of a filterable mercury precipitate when the sulfide content dropped below about 0.5 wt % and the pH was above 11. Results are summarized in Table 6.

TABLE 6

| | Time, min | | | | | | | |
|---|---|---|---|---|---|---|---|---|
| | 0 | 20 | 40 | 60 | 80 | 140 | 180 | 210 |
| pH | 11.74 | 11.85 | 12.07 | 11.5 | 11.72 | 11.6 | 11.69 | 5.17 |
| ml 30% H2O2 | 0.00 | 1.00 | 2.00 | 3.00 | 5.00 | 5.00 | 10.00 | 15.00 |
| Hg in Aqueous, ppbw | 8,970 | 8,713 | 8,797 | 8,850 | 8,753 | 8,990 | 8,403 | 7,807 |
| Hg after Filter, ppbw | 8,840 | 8,833 | 8,993 | 8,770 | 8,700 | 8,823 | 52 | 11 |
| % Hg in Aqueous | 100 | 97 | 98 | 99 | 98 | 100 | 94 | 87 |
| % Hg filterable | 1 | −1 | −2 | 1 | 1 | 2 | 99 | 100 |
| % Hg Recovery | 100 | 97 | 98 | 99 | 98 | 100 | 94 | 87 |
| % Hg Loss | 0 | 3 | 2 | 1 | 2 | 0 | 6 | 13 |

Example 51

The example illustrates removing dissolved mercury from ammonium sulfide solution by chemical oxidation. Example 48 procedures were followed to prepare a mercury-containing aqueous sulfidic solution that contained ~8,970 ppbw mercury. Example 49 was repeated except that 30% hydrogen peroxide was substituted for hydrochloric acid. The hydrogen peroxide consumed the stabilizing SH— anion and this resulted in precipitation of a filterable mercury precipitate when the total sulfide content dropped below about 0.1 wt % and the pH was above 8.5. A black residue was noted on the upper portion of the three-neck flask, which was assumed to be precipitated mercury and this accounted for the loss. Results are summarized in Table 7.

TABLE 7

| | Time, min | | | | | | | |
|---|---|---|---|---|---|---|---|---|
| | 0 | 30 | 60 | 90 | 120 | 180 | 210 | 240 |
| pH | 9.45 | 9.4 | 9.44 | 9.46 | 9.52 | 9.12 | 8.86 | 8.66 |
| ml 30% H2O2 | 0.00 | 1.00 | 2.00 | 3.00 | 5.00 | 10.00 | 15.00 | 20.00 |
| Hg in Aqueous, ppbw | 604 | 626 | 600 | 620 | 588 | 637 | 531 | 488 |
| Hg after Filter, ppbw | 596 | 586 | 607 | 521 | 593 | 618 | 26 | 6 |
| % Hg in Aqueous | 100 | 104 | 99 | 103 | 97 | 105 | 88 | 81 |
| % Hg filterable | 1 | 6 | −1 | 16 | −1 | 3 | 95 | 99 |
| % Hg Recovery | 100 | 104 | 99 | 103 | 97 | 105 | 88 | 81 |
| % Hg Loss | 0 | −4 | 1 | −3 | 3 | −5 | 12 | 19 |

Example 52

The example illustrates removing dissolved mercury from ammonium sulfide solution by chemical oxidation. The final product from Experiment 51 was passed through a series of filters and analyzed, with filter size of less than 10 μm. The results are in Table 8.

TABLE 8

| Filter size | ppbw | % Removed |
|---|---|---|
| None | 488 | 0 |
| 20 μm | 341 | 30 |
| 5 μm | 162 | 67 |
| 1 μm | 92 | 81 |

Example 53

The example illustrates removing dissolved mercury from ammonium sulfide solution by stripping, e.g., removing the stabilizing sulfide ions as hydrogen sulfide to precipitate mercury sulfide. The procedure of Example 48 was used to prepare a mercury-containing aqueous sulfidic solution that contained 6,387 ppbw mercury. About 300 grams of the solution was placed in a three neck flask equipped with a stir bar, nitrogen purge of 300 cc/min, a heating mantle, a reflux condenser equipped with tap water cooling, and a sampling port. This mercury could not be removed by a 1 μm filter. The solution was heated to 95° C. The ammonium sulfide was stripped out by the nitrogen purge. Samples were withdrawn and analyzed for mercury by a Lumex analyzer. A portion of the sample was filtered through a 1 μm filter to determine the amount of particulate Hg present. As the ammonium sulfide was stripped from the mercury-containing aqueous sulfidic solution the pH drops to below about 7.5 and the mercury can be removed by filtration. Results are summarized below in Table 9.

TABLE 9

| | Time, min | | | | | | | | | | |
|---|---|---|---|---|---|---|---|---|---|---|---|
| | 0 | 0 | 5 | 15 | 30 | 45 | 60 | 120 | 180 | 210 | 240 |
| pH | 9.57 | 9.23 | 9.11 | 9.01 | 8.95 | 8.81 | 8.8 | 8.32 | 7.68 | 7.34 | 6.9 |
| Temp. | 25 | 95 | 95 | 95 | 95 | 95 | 95 | 95 | 95 | 95 | 95 |
| Hg in Aqueous, ppbw | 6,387 | 6,517 | 6,783 | 6,607 | 6,823 | 6,593 | 6,550 | 6,400 | 2,937 | 2,180 | 1,950 |
| Hg after Filter, ppbw | 6,310 | 6,543 | 6,680 | 6,560 | 6,730 | 6,607 | 6,623 | 6,387 | 880 | 104 | 14 |
| % Hg in Aqueous | 100 | 75 | 78 | 76 | 78 | 76 | 75 | 73 | 34 | 25 | 22 |
| % Hg filterable | 1 | 0 | 2 | 1 | 1 | 0 | −1 | 0 | 70 | 95 | 99 |
| % Hg Recovery | 100 | 75 | 78 | 76 | 78 | 76 | 75 | 73 | 34 | 25 | 22 |
| % Hg Loss | 0 | 25 | 22 | 24 | 22 | 24 | 25 | 27 | 66 | 75 | 78 |

Example 54

This example illustrates removing dissolved mercury from ammonium sulfide solution by stripping. The final product from experiment 53 was passed through a series of filters and analyzed. The results are in Table 10.

TABLE 10

| Filter size | ppbw | % Removed |
|---|---|---|
| None | 2,250 | 0 |
| 20 μm | 829 | 63 |
| 5 μm | 800 | 64 |
| 1 μm | 144 | 94 |

Example 55

A simulated subsea pipeline was used to test the adsorption of vapor phase elemental mercury and then its subsequent removal by sulfidic solutions. Vapor phase elemental mercury was generated by reduction of mercuric chloride with stannous chloride in an acidic solution. 200 ml of a solution of stannous chloride and sulfuric acid was placed in a glass three-neck flask with a Teflon stirrer, for a concentration of 10% stannous chloride and 5% sulfuric acid. The solution was heated to 70° C. When mercury vapors were to be generated, 1.0 cc of a 203 ppm Hg solution of mercuric chloride in deionized water was injected into the reactor via a septum. The stannous chloride rapidly reduced the mercury to a pulse of 203 μg of elemental mercury. In the glass reactor was a line carrying 300 cc/min of nitrogen which bubbled in the reducing acidic stannous chloride solution. This was used to sweep the evolved elemental mercury to the downstream simulated pipeline. A two-foot ¼" stainless steel tube heated to 70° C. conveyed the mercury-containing gas from the three-neck flask to the simulated pipeline. The short distance and heating of this segment minimized the adsorption of elemental mercury prior to the simulated pipeline.

Several coils of one-foot diameter and fifty-foot in length of 316 stainless steel (SS) and AISI Grade 1010 (SAE J 403-95) cold-drawn seamless carbon steel (CS) tubing were provided. The tubings were ¼" OD with 0.035 inches wall thickness. The coiled tubings were immersed in a stainless steel container filled with chilled glycol maintained at 3° C. The gas exiting the chilled tubing was sent to a fritted bubbler filled with 200 ml of 3% sodium polysulfide solution in deionized water. This bubbler tapped any elemental mercury that was not adsorbed on the tubing.

All mercury measurements were performed by Lumex™. The limits of detection of the Lumex™ are about 50 ppb for liquid samples and about 500 μg/m$^3$ for gas phase samples.

Examples 56 to 60

The apparatus of example 58 was used in an adsorption and desorption experiments. In the adsorption phase of the experiment, pulses of 1 cc of the 203 ppm Hg solutions were injected into the three-neck flask. The mercury contents of gas leaving the reactor and the gases at the inlet and outlet of the adsorber were measured. The mercury contents of the reactor liquid and the adsorber liquid were also measured. Each pulse generated 203 μg of elemental mercury. These pulses were added in half-hour intervals until mercury was detected in the polysulfide bubbler in amounts greater than 500 ppb. Based on the density of elemental mercury (13.534 μm/cm$^3$) and the atomic radius of mercury in elemental mercury (151 μm), one monolayer of elemental mercury in the 50 foot long coil would contain approximately 895 μg. The adsorption of mercury in the coil was calculated from difference of the amount of mercury added in the pulses of mercury added and the amount of mercury found in the polysulfide bubbler. This amount of adsorbed mercury was expressed as both μg and as monolayer coverage (or fraction of a monolayer).

In the desorption phase of the experiment, sulfide solutions were pumped into the chilled coil at 20 ml/min and flowed in the opposite direction as the gas flow in the adsorption phase. The mercury content of the emerging sulfide solution was monitored over time, and the composite sulfide solution was weighed and analyzed for mercury. Two sulfide solutions were used for the desorption: 3% sodium sulfide in deionized water and 3% sodium polysulfide in deionized water. In some examples, one or the other sulfide agent was used and in some cases, both were used in sequence.

During the adsorption experiments, between 1 and 3 pulses of mercury were needed to see breakthrough. The gas and liquid phase mercury compositions reached steady values after thirty minutes if there was no breakthrough. If mercury was detected in the effluent from the coil (gas and liquid), the adsorption experiment continued until the gas and liquid phase analyses reached steady values.

During desorption the mercury was found to desorb quickly and often reached background detection limits (50 ppm) within 15 minutes. The sulfide solutions were flowed for a total of 30 minutes. Results are summarized in Table 12.

TABLE 12

| | | | | Adsorption | | | Desorption | | | | | |
| | | | | | | | 1st Desorption | | 2nd Desorption | | Total | |
| Example No | Metal | State | T, ° C. | Hg Ads., μg | Hg Ads. Mono-layers | Soln 1 | Hg Des., μg | Soln 2 | Hg Des., μg | Total Hg, μg | % Hg Removed |
|---|---|---|---|---|---|---|---|---|---|---|---|
| 56 | SS | Initial | 1 | 225 | 0.25 | Na$_2$S | 106 | Na$_2$S$_x$ | 106 | 212 | 94.33 |
| 57 | SS | Na$_2$S$_x$ | 3 | 58 | 0.06 | Na$_2$S | 31 | Na$_2$S$_x$ | 20 | 52 | 89.37 |
| 58 | CS | Initial | 3 | 432 | 0.48 | Na$_2$S | 67 | Na$_2$S$_x$ | 25 | 92 | 21.23 |
| 59 | CS | Na$_2$S$_x$ | 3 | 396 | 0.44 | Na$_2$S | 59 | None | 0 | 59 | 14.85 |
| 60 | CS | Na$_2$S | 5 | 4,093 | 4.57 | Na$_2$S | 1,820 | None | 0 | 1,820 | 44.47 |

In example 56, a new stainless steel coil adsorbed 225 µg of mercury, equivalent to 0.25 monolayers. Sodium sulfide and sodium polysulfide washes removed 94 percent of the mercury. The solutions remained their initial color and appearance: respectively water white and orange. The coil was then flushed with 1000 ml of deionized water. The mercury content of the deionized water was below the limit of detection. The coil was then dried overnight in flowing nitrogen.

Example 57 used the coil from example 56. Much less mercury was adsorbed, but all that was adsorbed was removed by the sodium sulfide and sodium polysulfide washes.

In example 58, a new carbon steel coil was found to adsorb 432 µg of mercury, equivalent to 0.48 monolayers. This is roughly twice the amount found for stainless steel. Sodium sulfide and sodium polysulfide washes removed 21 percent of the mercury. However the solutions did not maintain their initial color and appearance. The sodium sulfide was colorless but contained black particles. The sodium polysulfide was orange and also contained black particles. It is suspected that these black particles were an iron sulfide that also contained significant amounts of mercury. Thus the analysis of these solutions might have underestimated the amount of mercury removed by the solutions. The coil was then flushed with 1000 ml of deionized water. The mercury content of the deionized water was below the limit of detection. The coil was then dried overnight in flowing nitrogen.

Example 59 used the coil from example 58. Approximately the same amount of mercury was adsorbed. The desorption used only sodium sulfide and approximately 14% of the mercury was removed. However, the sodium sulfide solution contained black particles and the analysis of mercury removed might be an underestimate. The coil was then flushed with 1000 ml of deionized water. The mercury content of the deionized water was below the limit of detection. The coil was then dried overnight in flowing nitrogen.

Example 60 used the coil from example 59. The uptake of mercury was ten times higher than the value found in example 59. Sodium sulfide is preferred over sodium polysulfide as a final treatment of carbon steel as sodium sulfide enhances the ability to adsorb mercury. The desorption used only sodium sulfide and approximately 44% of the mercury was removed. The total was time was 50 minutes. The sodium sulfide solution contained black particles and the analysis of mercury removed might be an underestimate. The coil was then flushed with 1000 ml of deionized water. The mercury content of the deionized water was at the limit of detection. The spent sodium sulfide solution was filtered through a 0.45 micron filter. The mercury content of the filtrate was 2176 ppb, which was slightly higher than the starting sodium sulfide (1824 ppb). The filter collected 0.2208 grams of solids containing 212,000 ppb of mercury. This is equivalent of 47 micrograms. Thus while mercury was accumulating in the precipitated solids, this was not a major part of the mercury in solution.

For the purposes of this specification and appended claims, unless otherwise indicated, all numbers expressing quantities, percentages or proportions, and other numerical values used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent.

As used herein, the term "include" and its grammatical variants are intended to be non-limiting, such that recitation of items in a list is not to the exclusion of other like items that can be substituted or added to the listed items. The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof Unless otherwise defined, all terms, including technical and scientific terms used in the description, have the same meaning as commonly understood by one of ordinary skill in the art to which this invention belongs.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

The invention claimed is:

1. A process for producing a produced fluid having a reduced concentration of mercury from a pipeline, comprising:
   transporting a produced fluid containing mercury along the pipeline for a sufficient amount of time for the mercury to accumulate in the pipeline as elemental mercury, mercury sulfide and combinations thereof, wherein a sufficient amount of mercury accumulates on the pipeline reach a first mercury concentration at a check point downstream from an entry point of the produced fluid into the pipeline; stopping the transport of the produced fluid in a section of the pipeline; injecting a leading pig into the pipeline;
   injecting a composition comprising an aqueous sulfidic solution comprising at least 0.1 wt. % of any of a sulfide, a polysulfide, and combinations thereof, forming a first slug at rear of the leading pig, wherein the aqueous sulfidic solution reacts with elemental mercury accumulated on the pipeline along the first slug forming soluble mercury complexes in the aqueous sulfidic solution;
   injecting a first trailing pig into the pipeline at rear of the first slug; resuming flow of the produced fluid; and
   recovering the produced fluid having a mercury concentration of less than 50% of the first mercury concentration at a location downstream from the first slug.

2. The process of claim 1, wherein the leading pig is propelled by any of hydraulic pressure, a cable along a length of the pipeline, and flow of the produced fluid in the pipeline.

3. The process of claim 1, prior to resuming flow of the produced fluid, further comprising:
   injecting a flushing solution at rear of the first trailing pig, wherein the flushing solution displaces the aqueous sulfidic solution and forms a second slug at rear of the first trailing pig; and injecting a second trailing pig into the pipeline at rear of the first slug.

4. The process of claim 1, prior to resuming flow of the produced fluid, further comprising draining the aqueous sulfidic solution containing anionic mercury complexes from the pipeline.

5. The process of claim 1, wherein the aqueous sulfidic solution comprises 0.1 wt % to 25 wt % of any of a sulfide, a polysulfide, and combinations thereof.

6. The process of claim 5, wherein the mercury accumulated on the pipeline comprises mercuric sulfide, and wherein the mercuric sulfide dissolves in the aqueous sulfidic solution to form soluble mercury complexes is selected from $HgS_xH$, $HgSx^{-2}$ and combinations thereof, and wherein x>=2.

7. The process of claim 6, wherein the soluble mercury complexes are selected from $HgS_2H-$ and $HgS_2^2$.

8. The process of claim 7, wherein the mercury accumulated on the pipeline comprises elemental mercury, and wherein the elemental mercury is oxidized by and dissolved in the aqueous sulfidic solution to form soluble mercury complexes of $HgS_xH^-$ wherein x>=2.

9. The process of claim 1, wherein the aqueous sulfidic solution comprises at least 0.1 wt. % of an inorganic sulfide.

10. The process of claim 1, wherein the aqueous sulfidic solution comprises at least 0.1 wt. % of any of an inorganic polysulfide.

11. The process of claim 1, wherein the produced fluid downstream from the first slug has a mercury concentration of less than 30% of the first mercury concentration.

12. The process of claim 1, wherein the produced fluid downstream from the first slug has a mercury concentration of less than 10% of the first mercury concentration.

13. The process of claim 1, wherein the transport of the produced fluid is stopped after the first mercury concentration reaches a pre-determined level.

14. The process of claim 1, wherein the transport of the produced fluid is stopped after the produced fluid is transported in the pipeline for a pre-determined period of time.

15. The process of claim 1, wherein the transport of the produced fluid is stopped when the pipeline is scheduled for regular pigging maintenance.

16. The process of claim 1, further comprising:
recovering the aqueous sulfidic solution containing anionic mercury complexes.

17. The process of claim 16, further comprising:
precipitating mercuric sulfide from the aqueous sulfidic solution containing soluble mercury complexes by any of titration, oxidation, stripping, heating, distillation and combinations thereof; and
separating the precipitated mercuric sulfide from the aqueous sulfidic solution; and
recovering the aqueous sulfidic solution.

18. The process of claim 16, further comprising injecting the aqueous sulfidic solution containing soluble mercury complexes into an underground formation.

19. The process of claim 16, further comprising depositing precipitated mercuric sulfide into an underground formation.

20. A process for producing a produced fluid having a reduced concentration of mercury from a pipeline, comprising:
transporting a produced fluid containing mercuric sulfide along the pipeline for a sufficient amount of time for the mercuric sulfide to accumulate in the pipeline as elemental mercury, mercury sulfide and combinations thereof, wherein one of elemental mercury, mercury sulfide and combinations thereof accumulates on the pipeline for the produced fluid to reach a first mercury concentration of one of elemental mercury, mercury sulfide and combinations thereof-at a check point downstream from an entry point of the produced fluid into the pipeline;
stopping the transport of the produced fluid in a section of the pipeline;
injecting a leading pig into the pipeline, wherein the leading pig is propelled by hydraulic pressure or flow of the produced fluid in the pipeline;
injecting a composition comprising at least 0.1 wt. % of an inorganic sulfide, and combinations thereof, forming a first slug at rear of the leading pig, wherein the inorganic sulfide reacts with the mercuric sulfide accumulated on the pipeline along the first slug forming anionic mercury complexes of $HgS_2H-$ and $HgS_2^2$;
injecting a first trailing pig into the pipeline at rear of the first slug;
resuming flow of the produced fluid; and
recovering the produced fluid having a mercury concentration of less than 50% of the first mercury concentration at a location downstream from the first slug.

21. A process for producing a produced fluid having a reduced concentration of mercury from a pipeline, comprising:
transporting a produced fluid containing elemental mercury ($Hg^0$) along the pipeline for a sufficient amount of time for the elemental mercury to accumulate in the pipeline as elemental mercury, mercury sulfide and combinations thereof, wherein one of elemental mercury, mercury sulfide and combinations thereof, accumulates on the pipeline for the produced fluid to reach a first mercury concentration of one of elemental mercury, mercury sulfide and combinations thereof, at a check point downstream from an entry point of the produced fluid into the pipeline;
stopping the transport of the produced fluid in a section of the pipeline; injecting a leading pig into the pipeline, wherein the leading pig is propelled by hydraulic pressure or flow of the produced fluid in the pipeline;
injecting a composition comprising at least 0.1 wt. % of an inorganic polysulfide, and combinations thereof, forming a first slug at rear of the leading pig, wherein the inorganic polysulfide reacts with the elemental mercury accumulated on the pipeline along the first slug forming soluble mercury complexes of HgS2H—;
injecting a first trailing pig into the pipeline at rear of the first slug; resuming flow of the produced fluid; and
recovering the produced fluid having a mercury concentration of less than 50% of the first mercury concentration at a location downstream from the first slug.

22. The method of claim 21, wherein the inorganic polysulfide is selected from the group of sodium polysulfide, ammonium polysulfide, potassium polysulfide, calcium polysulfide, sulfanes ($H_2Sx$), and mixtures thereof.

* * * * *